United States Patent [19]

Young

[11] 4,447,642

[45] * May 8, 1984

[54] PREPARATION OF ALKYL CARBOXYLATES

[75] Inventor: Lewis B. Young, Skillman, N.J.

[73] Assignee: Mobil Oil Corporation, New York, N.Y.

[*] Notice: The portion of the term of this patent subsequent to Dec. 21, 1999 has been disclaimed.

[21] Appl. No.: 429,937

[22] Filed: Sep. 30, 1982

Related U.S. Application Data

[63] Continuation-in-part of Ser. No. 217,979, Dec. 19, 1980, Pat. No. 4,365,083.

[51] Int. Cl.$^3$ .............................................. C07C 67/04
[52] U.S. Cl. ............................. 560/247; 260/410.9 R
[58] Field of Search ................... 560/247; 260/410.9 R

[56] References Cited

U.S. PATENT DOCUMENTS

| | | | |
|---|---|---|---|
| 3,014,066 | 12/1961 | Kerr | 560/247 |
| 3,085,108 | 4/1963 | Stepanek | 560/247 |
| 3,096,365 | 7/1963 | Heisler | 560/247 |
| 3,492,341 | 1/1970 | Trevillyan | 560/247 |
| 4,365,083 | 12/1982 | Young | 560/247 |

*Primary Examiner*—Michael L. Shippen
*Attorney, Agent, or Firm*—McKillop A. J.; M. G. Gilman; E. F. Kenehan, Jr.

[57] ABSTRACT

A process for preparation of alkyl carboxylate mixtures enriched in alpha-methylalkyl carboxylate compounds, by reaction of an olefin and a carboxylic acid compound in the presence of a mordenite catalyst.

6 Claims, No Drawings

PREPARATION OF ALKYL CARBOXYLATES

CROSS-REFERENCE TO RELATED APPLICATION

This application is a continuation-in-part of the copending application of Lewis B. Young, said application having Ser. No. 217,979, filed Dec. 19, 1980, now U.S. Pat. No. 4,365,083.

BACKGROUND OF THE INVENTION

1. Field of the Invention

This invention is concerned with the preparation of alkyl carboxylate mixtures which are enriched in alpha-methylakyl carboxylates. Such mixtures are prepared by reaction of carboxylic acids with olefinic compounds in the presence of a particular type of crystalline zeolite catalyst.

2. Description of the Prior Art

The addition of carboxylic acids to olefins to make esters is known. The chemical literature describes the use of Lewis acid catalysts, such as $BF_3$, to promote the reaction. However, particularly in the case of internal olefins, the reaction will result in addition of the carboxylic acid to both ends of the double bond, thereby giving rise to a mixture of carboxylate products. Mineral acids (e.g., $H_2SO_4$) are also reported to catalyze the reaction, but the result is much the same, i.e., non-selective addition of the carboxylic acid to either side of the carbon-carbon double bond. Trevillyan; U.S. Pat. No. 3,492,341, issued Jan. 27, 1970 discloses preparation of alkyl carboxylate esters by reacting carboxylic acids with 1- or 2-monoolefins over a mordenite zeolite catalyst.

In the past, the only known reaction route to directly produce alkyl carboxylate mixtures enriched in alpha-methylalkyl carboxylates has required the utilization of expensive alpha-olefins. Reaction with internal or mixed olefins using common acid catalysts has necessitated physical separation of the isomeric variants of the alkyl carboxylate product by other means, such as distillation, in order to isolate a product which is rich in the alpha-methylalkyl carboxylate.

Alkyl esters of carboxylic acids are useful as solvents, plasticizers and chemical intermediates. Alpha-methylalkyl carboxylates are particularly useful for making secondary alcohols with hydroxyl attachment at the 2-carbon. By utilization of the herein disclosed method, alpha-methylalkyl carboxylate enriched products normally derived from pure alpha-olefins can now be prepared from less expensive linear olefin mixtures.

SUMMARY OF THE INVENTION

It has now been discovered that certain zeolite materials may be utilized to promote reaction between olefins and carboxylic acids to produce an alkyl carboxylate reaction product enriched in alpha-methylalkyl carboxylate isomers. In a particularly preferred embodiment, alpha-methylalkyl carboxylates are prepared as the major alkyl carboxylate product from the reaction of carboxylic acids and internal linear olefins or olefin mixtures containing significant amounts of internal olefins. Specifically, the alpha-methylalkyl carboxylates contemplated herein as the principal alkyl carboxylate product are those described by the formula:

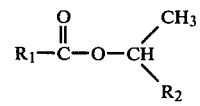

wherein:
$R_1$ = alkyl, aryl, haloalkyl or hydrogen, and preferably = alkyl of 1 to 10 carbons; and
$R_2$ = $C_1$–$C_{20}$ alkyl, heteroalkyl or cycloalkyl, and preferably = $C_4$–$C_{18}$ alkyl.

The method comprises reacting a carboxylic acid having the formula

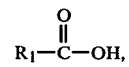

$R_1$ being described above, with an olefin having from 3 to about 20 carbon atoms. Substantially any linear, slightly branched, cyclic or heteroatom-substituted olefin may be employed, regardless of the position of the carbon-carbon double bond. However, linear olefins are preferred. In a particularly preferred embodiment, olefin mixtures are utilized wherein such mixtures contain at least 25 mole percent of a $C_6$–$C_{20}$ olefin having no unsaturation at the site of the No. 2 carbon atom of the olefin.

A wide range of temperature and pressure conditions are found to be conductive to the reaction, which may be successfully carried out at 25° C. to 600° C. and $10^4$ Pa to $10^7$ Pa (0.1 to 100 atmospheres) pressure. Temperatures of between 75° C. and 400° C. are preferred, as are pressures of $10^5$ Pa to $40 \times 10^5$ Pa (1 to 40 atmospheres). The reaction may be usefully carried out in either the liquid or vapor phase, although it may be found preferable to employ liquid phase reaction.

The particular zeolite material employed to promote the novel, selective addition reaction of this invention is the zeolite mordenite. The mordenite may be synthetically prepared or naturally occurring. De-aluminized mordenites, i.e. those subjected to acid treatment to increase the silica to alumina mole ratio to a relatively high level, are preferred.

DESCRIPTION OF SPECIFIC EMBODIMENTS

A one-step process has now been found for the manufacture of alkyl carboxylates from carboxylic acids and olefins, with especially desirable selectivity to production of an alpha-methylalkyl carboxylate enriched product. By utilization of the particular zeolite catalyst described hereinafter, it now becomes possible to react carboxylic acids with olefins having the carbon-carbon double bond in substantially any position in the molecule and produce an adduct wherein the carboxylate has attached principally at the #2 carbon of the olefin molecule. This is in striking contrast to the reaction product resulting from utilization of Lewis acid and mineral acid catalysts wherein the carboxylate would attach at the carbons on either side of the double bond and, unless the site of the unsaturation included the #2 carbon atom, the resultant yield of alpha-methylalkyl carboxylates in the alkyl carboxylate reaction product would comprise no more than a minor byproduct.

The carboxylic acids useful in the process of the present invention are preferably alkyl carboxylic acids having from 1 to about 10 carbon atoms therein. Included within this group are, for example, formic acid, acetic acid, propionic acid, butyric acid and hexanoic acid. Slightly branched alkyl carboxylic acids are also useful, such as, for instance, isobutyric acid. Haloalkyl carboxylic acids, such as chloroacetic acid, fluoroacetic acid and trifluoroacetic acid may be employed. Also, aryl carboxylic acids will be found desirable in some instances, including benzoic acid, para-toluic acid and para-chlorobenzoic acid. For commercially viable applications, it is expected that acetic acid will be found particularly desirable.

Olefins suitable for manufacture of alpha-methylalkyl carboxylate enriched carboxylate mixtures as described herein are not limited to alpha-olefins. Rather, it has been found that substantially any olefinic hydrocarbons may be employed without regard to the location of the site of unsaturation. Mixed isomers of a given olefin are particularly desirable due to their ready availability and relatively low cost. Linear $C_3$–$C_{20}$ olefins are especially preferred, but slightly branched olefins may also be employed. Some non-limiting examples include propylene, butene, octene, dodecene, hexadecene and 1-methylnonene. Especially preferred olefinic reactants are olefin mixtures containing at least 25% of a $C_6$–$C_{20}$ olefin having no unsaturation at the site of the No. 2 carbon atom thereof. It is especially surprising that internal olefins of this type can comprise a substantial part or even all of the olefinic reactant and still have the resulting alkyl carboxylate product enriched in the alpha-methylalkyl carboxylate.

The zeolite material utilized as the catalyst in the process of this invention is known as mordenite. This zeolite is naturally occurring and, in its natural state, normally has a silica to alumina mole ratio approximately equal to 5–10. 1 However, a large part of the alumina can be removed from the mordenite crystal framework, thereby substantially increasing the silica to alumina mole ratio, by acid extraction or "leaching". This increases the effective pore diameter and thus diffusivity of reactant and product molecules to and from the active sites. Acid extraction, commonly referred to as de-aluminization of the zeolite, is generally accomplished by treatment with strong mineral acids which, in addition to removing $Al_2O_3$, also replace metal cations (e.g. $Na^+$) with hydrogen ions. In the process of the hereindisclosed invention, the utilization of de-aluminized mordenites is preferred.

Mordenite can also be prepared synthetically. One method of synthesis is disclosed by L. B. Sand in U.S. Pat. No. 3,436,174. Another will be found in U.S. Pat. No. 3,574,539, issued to D. Domine and J. Quobex. Both patents are incorporated herein by reference for the purpose of showing synthetic methods of mordenite preparation.

In practicing the alkyl carboxylate production process of the present invention, it may be useful to incorporate the above-described crystalline zeolite with a matrix comprising another material resistant to the temperature and other conditions employed in the process. Such matrix material is useful as a binder and imparts greater resistance to the catalyst for the severe temperature, pressure and reactant feed stream velocity conditions encountered in some processes.

Useful matrix materials include both synthetic and naturally occurring substances, as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix, on an anhydrous basis, may vary widely with the zeolite content ranging from between about 1 to about 99 percent by weight and more usually in the range of about 5 to about 80 percent by weight of the dry composite.

The process of this invention is carried out such that the organic reactants, i.e., the carboxylic acid and the olefinic reactant, are brought into contact with the particular type of zeolite material described herein in a suitable reaction zone under alkyl carboxylate ester forming reaction conditions. Such conditions include a temperature which is elevated to a level conducive to the addition reaction. Suitable temperatures are from about 25° C. to about 600° C., but temperatures of between 75° C. and 400° C. are preferred. The reaction zone will preferably be pressurized to approximately $10^5$ Pa to $40 \times 10^5$ Pa (1 to 40 atmospheres) pressure, but pressures falling within the range of $10^4$ Pa to $10^7$ Pa (0.1 to 100 atmospheres) will be found to be utilizable.

The ester-forming process described herein may be carried out as a batch-type, semi-continuous or continuous operation utilizing a fixed or moving bed catalyst system. A preferred embodiment entails use of a catalyst zone wherein the organic charge is passed concurrently or countercurrently through a moving bed of particle-form catalyst. The latter, after use, is conducted to a regeneration zone where coke is burned from the catalyst in an oxygen-containing atmosphere (such as air) at elevated temperature, after which the regenerated catalyst is recycled to the conversion zone for further contact with the organic reactants.

By utilization of the particular type of zeolite catalyst and reaction conditions described hereinbefore, it now becomes possible to react carboxylic acids with olefinic hydrocarbons which have the carbon-carbon double bond in substantially any position in the molecule and to nevertheless selectively produce an alkyl carboxylate reaction product enriched in the alpha-methylalkyl carboxylate isomer. For purposes of the present invention, the alkyl carboxylate product is enriched in alpha-methylalkyl carboxylate wherein the alpha-methylalkyl isomer comprises at least 40% of the total alkyl carboxylate product. Preferably the alpha-methylalkyl isomer comprises at least 50% or even at least 60% of the total alkyl carboxylate product.

The following examples are provided to illustrate the process of this invention and to aid those in the art in the understanding thereof, but clearly should not be taken as presenting undue limitations thereon:

EXAMPLE 1

A sample of a commercially available mordenite zeolite catalyst (Zeolon 500) was de-aluminized by extraction with 0.5 N HCl to adjust the silica to alumina mole ratio to approximately 85. One-tenth of a gram of the dried, de-aluminized zeolite was ground to a powder and added to 10 ml of a mixture of 1-decene and acetic acid (mole ratio=1:4). The mixture was heated to reflux and samples were periodically removed and analyzed. As will be seen from the summary provided in TABLE I, the product of the reaction was overwhelmingly the 2-isomer (2-decylacetate) with minor amounts of the 3-, 4- and 5-isomers as byproducts.

TABLE I

| Reaction Of 1-Decene And Acetic Acid | | | |
|---|---|---|---|
| Temperature | 120° C. | 120° C. | 120° C. |
| Reaction Time, hrs. | 1 | 25 | 47 |
| $C_{10}$ Product Distribution | | | |
| $C_{10}H_{20}$ | 65 wt % | 29 wt % | 29 wt % |
| $C_{10}H_{21}OAc$ | 26 wt % | 58 wt % | 58 wt % |
| $(C_{10}H_{20})_2$ | 9 wt % | 13 wt % | 13 wt % |
| $C_{10}H_{21}OAc$ Isomer Distribution | | | |
| 2- | | 80% | 75% |
| 3- | | 19% | 23% |
| 4- | | 0.9% | 1.3% |
| 5- | | 0.2% | 0.3% |

EXAMPLE 2

Using another sample of the same mordenite catalyst, 1-octene and acetic acid (mole ratio=1:4) were reacted in the manner described in Example 1. The results of the analysis are shown in TABLE II. Again, it is seen that the 2-isomer (2-octylacetate) is selectively produced relative to the higher isomers.

TABLE II

| Reaction Of 1-Octene And Acetic Acid | | | |
|---|---|---|---|
| Temperature | 120° C. | 120° C. | 120° C. |
| Reaction Time, hrs. | 2.5 | 5 | 23 |
| $C_8$ Product Distribution | | | |
| $C_8H_{16}$ | 61.6 wt % | 47.9 wt % | 36.6 wt % |
| $C_8H_{17}OAc$ | 31.7 wt % | 45.5 wt % | 57.8 wt % |
| $(C_8H_{16})_2$ | 6.7 wt % | 6.6 wt % | 5.6 wt % |
| $C_8H_{17}OAc$ Isomer Distribution | | | |
| 2- | 93.6% | 91.6% | 85.4% |
| 3- | 6.4% | 8.4% | 14.0% |
| 4- | — | — | 0.6% |

EXAMPLE 3

2-Octene and acetic acid (mole ratio=1:2) were reacted in the presence of the mordenite catalyst as described above. The results are summarized in TABLE III.

EXAMPLE 4 (COMPARATIVE)

A mixture of 2-octene and acetic acid (mole ratio=1:4) were reacted in the presence of a conventional Lewis Acid catalyst (boron trifluoride etherate). The reaction was carried out on a steam bath at 90° C. and samples were removed and analyzed at 1.2 and 2.7 hours. The results are given in TABLE III.

TABLE III

| Reaction Of 2-Octene And Acetic Acid | | | | | |
|---|---|---|---|---|---|
| Catalyst | Mordenite | | | $BF_3.Et_2O$ | |
| Temperature | 120° C. | 120° C. | 120° C. | 90° C. | 90° C. |
| Reaction Time, hrs. | 0.5 | 18 | 43 | 1.2 | 2.7 |
| Yield of $C_8OAc$, wt % | 19 | 60 | 59 | 37 | 57 |
| $C_8H_{17}Ac$ Isomer Distribution | | | | | |
| 2- | 64% | 64% | 63% | 52% | 52% |
| 3- | 36% | 34% | 34% | 45% | 44% |
| 4- | — | 2% | 3% | 3% | 4% |

A significant improvement in selectivity to the 2-isomer is seen for the reaction over the mordenite catalyst vis-a-vis the conventional $BF_3$—$Et_2O$ carboxylation catalyst.

EXAMPLE 5

A 1:2 molar ratio mixture of 4-octene and acetic acid was mixed with the mordenite catalyst of Example 1 and heated to reflux. Samples were taken at 4 and 22 hours and analyzed. The results are summarized in TABLE IV.

EXAMPLE 6 (COMPARATIVE)

For purposes of comparison, a mixture of 4-octene and acetic acid were heated on a steam bath to 90° C. in the presence of $BF_3$ $Et_2O$. The results of this reaction are also shown in TABLE IV.

TABLE IV

| Reaction of 4-Octene and Acetic Acid | | | | |
|---|---|---|---|---|
| Catalyst | Mordenite | | $BF_3$ | $Et_2O$ |
| Temperature | 120° C. | 120° C. | 90° C. | 90° C. |
| Reaction Time, hrs. | 4 | 22 | 0.6 | 4.3 |
| Yield of $C_8OAc$, wt % | 10 | 31 | 9 | 66 |
| $C_8H_{17}OAc$ Isomer Distribution | | | | |
| 2- | 31% | 41% | 1% | 8% |
| 3- | 46% | 38% | 5% | 18% |
| 4- | 23% | 20% | 94% | 75% |

As will be seen from the data, the conventional Lewis Acid catalyst resulted in an alkyl carboxylate product which was almost entirely the 4-isomer, as would normally be expected due to the location of the carbon-carbon double bond. In contrast, the mordenite zeolite catalyst provided a product mixture having only minor amounts of the 4-isomer and a substantial increase in the proportion of the 2- and 3-isomers. The selectivity to the 2-isomer is especially surprising in view of the internal position of the unsaturated site.

When in the Example 5 procedure, the 4-octene reactant is replaced by an octene mixture comprising 25% each of 1-octene, trans-2-octene, trans-3-octene, and trans-4-octene, substantial selectivity (i.e. at least 40% of alkyl carboxylate product) to production of the 2-$C_8H_{17}OAc$ isomer results.

Having thus described the present invention with the aid of certain specific examples thereof, it is to be understood that such examples are intended to be merely illustrative of the disclosed process. Many variations thereon may be made without departing from the spirit of the disclosed invention, as will be evident to those skilled in the art, and such variations are intended to come within the scope of the following claims:

What is claimed is:

1. A process for the preparation of alkyl carboxylate mixtures enriched in alpha-methylalkyl carboxylates of the formula:

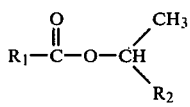

wherein $R_1$ is alkyl of 1 to 10 carbon atoms and $R_2$ is $C_4$–$C_{18}$ alkyl, said process comprising:
reacting an olefin mixture containing at least 25 percent of a $C_6$ to $C_{20}$ olefin having no unsaturation at the site of the No. 2 carbon atom thereof, with a $C_1$ to $C_{10}$ carboxylic acid, said reaction being carried out under ester-forming reaction conditions including the presence of a catalyst comprising the crystalline zeolite material mordenite, to thereby selectively produce an alkyl carboxylate ester product which is enriched in the alpha-methylalkyl carboxylate ester.

2. The process of claim 1 wherein said ester-forming reaction conditions include a temperature of between about 25° C. and 600° C. and at a pressure of within the range of $10^4$ Pa to $10^7$ Pa.

3. The process of claim 2 wherein said carboxylic acid is selected from acetic acid, propionic acid and butyric acid.

4. The process of claim 1 wherein the olefins in said olefin mixture are linear or slightly branched and have from 3 to about 20 carbon atoms therein.

5. The process of claim 1, 2, 3 or 4 wherein said mordenite zeolite is dealuminized.

6. The process of claim 5 wherein said zeolite additionally comprises a binder therefor.

* * * * *